(12) United States Patent
Kopp et al.

(10) Patent No.: US 11,547,775 B2
(45) Date of Patent: Jan. 10, 2023

(54) ASSEMBLY COMPRISING A RESORBABLE MATERIAL HAVING ANTIBACTERIAL ACTIVITY

(71) Applicant: MEOTEC GmbH & Co. KG, Aachen (DE)

(72) Inventors: Alexander Kopp, Aachen (DE); Francesco D'Elia, Aachen (DE); Ralf Smeets, Hamburg (DE)

(73) Assignee: Meotec GmbH & Co. KG, Aachen (DE)

( * ) Notice: Subject to any disclaimer, the term of this patent is extended or adjusted under 35 U.S.C. 154(b) by 824 days.

(21) Appl. No.: 16/474,597

(22) PCT Filed: Dec. 20, 2017

(86) PCT No.: PCT/EP2017/083826
§ 371 (c)(1),
(2) Date: Jun. 28, 2019

(87) PCT Pub. No.: WO2018/122066
PCT Pub. Date: Jul. 5, 2018

(65) Prior Publication Data
US 2019/0321513 A1    Oct. 24, 2019

(30) Foreign Application Priority Data

Dec. 28, 2016 (DE) .................. 10 2016 125 816.4
Mar. 20, 2017 (DE) .................. 10 2017 204 627.9

(51) Int. Cl.
*A61L 27/04* (2006.01)
*A61L 17/06* (2006.01)
(Continued)

(52) U.S. Cl.
CPC ...... *A61L 27/047* (2013.01); *A61B 17/06166* (2013.01); *A61C 8/0012* (2013.01);
(Continued)

(58) Field of Classification Search
CPC .................. A61B 17/06166; A61C 8/0012
See application file for complete search history.

(56) References Cited

U.S. PATENT DOCUMENTS

| 2,094,578 A | 10/1937 | Blumenthal et al. |
| 5,765,740 A | 6/1998 | Ferguson |

(Continued)

FOREIGN PATENT DOCUMENTS

| CN | 202122594 U | 1/2012 |
| CN | 103614601 A | 3/2014 |

(Continued)

OTHER PUBLICATIONS

"Aquatreat AR-708" Accessed online on May 11, 2022 at <https://www.nouryon.com/product/aquatreat-ar-708-phosphinocarboxylic-acid-pca/>. (Year: 2022).*

(Continued)

*Primary Examiner* — Carlos A Azpuru
*Assistant Examiner* — Casey S Hagopian
(74) *Attorney, Agent, or Firm* — Rankin, Hill & Clark LLP

(57) ABSTRACT

The invention relates to an arrangement (1) comprising at least one structural element (2) made of an absorbable material with an antibacterial effect with a mount, which possesses an aspect ratio greater than 10 and whereat the material is a rapidly corroding magnesium alloy. The invention further relates to a mount (10) with an arrangement (1) carried by the mount (10) comprising at least one structural element (2) made of an absorbable material with an antibacterial effect.

16 Claims, 4 Drawing Sheets

Figure 1:
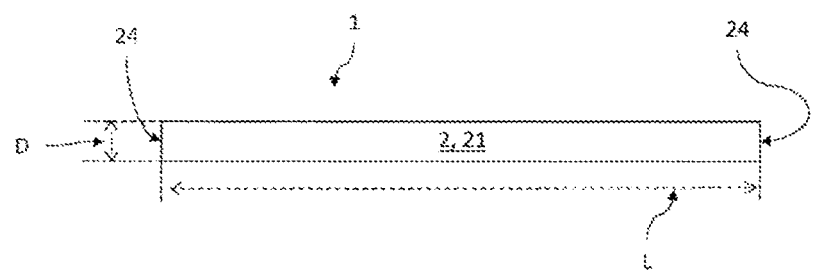

(51) Int. Cl.
    *A61L 27/34*     (2006.01)
    *A61L 27/54*     (2006.01)
    *A61L 27/58*     (2006.01)
    *A61B 17/06*     (2006.01)
    *A61C 8/00*     (2006.01)
    *A61K 6/70*     (2020.01)

(52) U.S. Cl.
    CPC ............... *A61K 6/70* (2020.01); *A61L 17/06* (2013.01); *A61L 27/042* (2013.01); *A61L 27/34* (2013.01); *A61L 27/54* (2013.01); *A61L 27/58* (2013.01); *A61L 2300/102* (2013.01); *A61L 2300/104* (2013.01); *A61L 2300/404* (2013.01); *A61L 2300/604* (2013.01)

(56) References Cited

U.S. PATENT DOCUMENTS

| | | | | |
|---|---|---|---|---|
| 2012/0041483 | A1* | 2/2012 | Indiano | A61B 17/06166 606/228 |
| 2012/0053567 | A1* | 3/2012 | Schreck | A61B 17/24 604/514 |

FOREIGN PATENT DOCUMENTS

| | | | |
|---|---|---|---|
| CN | 104511048 A | * | 4/2015 |
| CN | 104511048 A | | 4/2015 |
| CN | 104513922 A | | 4/2015 |
| CN | 105349858 A | | 2/2016 |
| DE | 102007063317 A1 | | 7/2009 |
| KR | 20160142667 A | | 12/2016 |
| WO | 2013176769 A1 | | 11/2013 |

OTHER PUBLICATIONS

Machine translation of CN-104511048-A, Apr. 2015. (Year: 2015).*
"Rare Earth Metals" Accessed online on May 12, 2022 at <https://simplifiedupsc.in/>. (Year: 2022).*
D. Tie et al. "Antibacterial biodegradable Mg—Ag alloys," European cells & materials, Jun. 2013, pp. 284-298, vol. 25, ReasearchGate, Germany.
Yang Li et al. "Biodegradable Mg—Cu alloy implants with antibacterial activity for the treatment of osteomyelitis: In vitro and in vivo evaluations," Biomaterials, 2016, pp. 250-263, vol. 106, Elsevier, The Netherlands; Cited in ISR.
Muhammad Imran Rahim et al. "Alkalization is responsible for antibacterial effects of corroding magnesium," Journal of Biomedical Materials Research A, Nov. 2015, p. 3526-3532, vol. 103A issue 11, Wiley Periodicals, USA; Cited in ISR.
Goodfellow "Magensium Goodfellow Catalogue," pp. 1-31 (pp. 9 and 27 cited), Retrieved from Internet: URL: http://www.goodfellow.com/pdf/4611_1111010.pdf; Cited in ISR.
Frank Witte "The history of biodegradable magnesium implants: A review," Acta Biomaterialia, 2010, pp. 1680-1692, vol. 6 No. 5, Elsevier, The Netherlands; Cited in ISR.
International Search Report dated Mar. 20, 2019 file in PCT/EP2017/083826.

* cited by examiner

ASSEMBLY COMPRISING A RESORBABLE MATERIAL HAVING ANTIBACTERIAL ACTIVITY

FIELD OF THE INVENTION

The invention relates to an arrangement comprising at least one structural element made of an absorbable material with an antibacterial effect and a mount for providing this arrangement.

BACKGROUND OF THE INVENTION

Due to contamination, for instance from a short or long-term insertion of a foreign body, an inflammatory reaction may occur in a body of an animate being. In particular, among specific medical products that are exposed to the otherwise sterile bone, such inflammation may occur, which needs to be treated or else implant incorporation may worsen or the organism in its entirety may be threatened. Bone inflammation is an inflammation of bone matter. In everyday use, the term bone inflammation is generally used for inflammation of the outer, harder bone matter as well as the bone marrow. Physicians differentiate though precisely between an inflammation of the solid substance of a bone (osteitis), with no inclusion of the bone marrow and an inflammation of the bone marrow (Osteomyelitis). Osteitis and osteomyelitis are in most cases caused by bacteria (very rarely by viruses or fungi) and occur after bone fractures (fractures), surgery on the bone or infections. Bone inflammation may occur, if bacteria from outside reach the bone, for example on an open wound or a surgery wound. The affected particular bone is dependent on the location of the aetiologic wound. Often affected are thigh (femur) and shank (tibia).

An often occurring exception of previously described inflammation is periimplantitis. This refers to an inflammation of soft- and hard tissue of implant beds around dental implants. The preliminary phase to periimplantitis is mucositis, an inflammation of the implant neck surrounding mucous membrane. Periimplantitis becomes noticeable through bleedings and advancing bone loss around the implant. If untreated, it leads to an increased mobility of the implant and a possible implant failure due to lacking of sufficient anchorage of the implant. Inflammations due to periimplantitis are diagnosed for 10%-45% of all dental implants within 10 years after implantation. Thus, periimplantitis is a continuing medical problem, which is not easily treated. Proliferation and advance of periimplantitis is due to the existence of bacterial biofilm. Growing of biofilms represents the preferred method of reproduction among most bacteria and contributes to their development of resistance.

It has been shown that silver and silver alloys may be used to effectively suppress bacterial proliferation, as these materials destroy the DNA of both gram-positive and gram-negative bacteria. For adding silver in different conditions to titan implants several techniques were tested, for example ion implantation, physical gas vapor deposition (PVD), sputter and plasma electrolytic oxidation and qualification of silver as antibacterial coating, in order to prevent bone loss caused by periimplantitis, was determined. But even if the application of silver coatings prevents attachment and colonization of bacteria, such coatings increase surface roughness of implants. An increased roughness of exemplarily more than 0.2 µm is known to support proliferation of biofilms and thus may support a spontaneous advance of periimplantitis.

Magnesium silver alloys were also investigated as antibacterial effective implants. This alloy was non-corrosive and displayed satisfactory mechanical characteristics and a neglectable cytotoxicity and an antibacterial activity. Absorbable materials may however be unsuitable for some implants, as these possess no longtime stability and, for example, dental implants are designed as permanent applications.

It would therefore be desirable, to possess a qualified mean, which allows a simple provision of implants without elaborate modification, and which effectively suppress or combat the threat of inflammation, for example periimplantitis, after implantation.

SUMMARY OF THE INVENTION

It is therefore a task of the present invention to provide a qualified mean, that can be provided easily and without elaborate modification and is suitable to suppress or combat an inflammatory reaction in the body of an animate being, after introduction.

This task is solved by an arrangement comprising at least one structural element made of an absorbable material with an antibacterial effect with a form, which has an aspect ratio greater than 10 and whereby the material is a rapidly corroding magnesium alloy.

The aspect ratio describes a relation between the height of a structure and its smallest lateral expansion. In a thread shaped structure the structure height resembles the thread length and the smallest lateral expansion of the diameter of the cross section of the thread shaped structure perpendicular to its length. A structural element with an aspect ratio of at least 10 designates a thread shaped structural element, which is exemplarily produced by wire drawing, extrusion, punching, laser- or waterjet-cutting.

A material is designated absorbable, if the material dissolves in a body's environment of a respective organism and if the material is at least partially absorbed by the organism.

Arrangements made of magnesium are therefore outstandingly qualified as an implant. Here, resorption is a specific material characteristic and also a function of time. Magnesium is well absorbable in the human body, due to its natural presence as a mineral in most body cells and magnesium or magnesium alloys are significantly harder than, for example, resorbable polymers. The arrangement according to the invention is designed for deposition in the human body and thus represents a supporting implant. Such magnesium-implants may be absorbed by the body. Therefore, implants made of magnesium do not remain as a foreign body in the human body and possible later complications are prevented.

The term magnesium alloy is understood as a material, which consists mainly of magnesium, but may also contain other materials. These may represent a small fraction, for example less than 0.1% in weight, but also represent a greater fraction above 0.1% in weight. Also pure magnesium without any other constituents, or merely representing a slender fraction of such, is understood to be a magnesium alloy.

The term "corrosion" describes a reaction of a material to its environment, which causes an alteration of the material and either decomposes or erodes it. A corrosion caused by an animated being is designated a biocorrosion. Corrosion rate is the pace of material alteration resp. material leveling and defines rapidity of corrosion. It is essentially dependent on corresponding substance concentration, pH value of the environment and temperature. Here, the term rapidly corroding relates to material alteration in an aqueous environment at a pH value between 4 and 8 (acidic to neutral resp. slightly basic) at room temperature to body temperature (37°-38° C.). A rapid corrosion, according to the present invention, is understood to be present when the normalized or plane- or volume dependent accelerated or real in-vitro or in-vivo corrosion rate is above 1 mm loss of material thickness per year (as mm/year). In this context even higher corrosion rates, for example more than 2 mm/year, 3 mm/year, 4 mm/year, 5 mm/year or 10 mm/year are understood as rapidly corroding. Usually, the state of art reduces, for example, the iron content in magnesium alloys to a minimum, for example smaller than 50 ppm, in order to prevent a corrosion of the respective magnesium alloy.

A material of a substance with an antibacterial effect reduces the reproductive effect of micro organsisms (bacteria), kills them or deactivates them for example through biological, chemical, mechanical or thermal damage.

During degradation of magnesium in an aqueous environment as the body, hydrogen gas always develops due to the reaction. In small quantities, resp. at moderate release, this has no effect. If the degradation is sufficiently rapid and/or occurs on a structural element which reaches a sufficiently large surface and a specific amount of hydrogen gas, resp. a sufficient rate of release is achieved, the amount of hydrogen gas itself acts antibacterial. Due to the rapid corrosion of the magnesium alloy the quantity of hydrogen gas required for the antibacterial effect is generated. If the degradation takes place excessively or furthermore in closed tissue sections, the release may lead to the creation of gas pockets, which are not desired and must be avoided. Therefore, degradation of the implant respectively its corrosion rate must be designed according to the function. At a slow corrosion the antibacterial effect of the magnesium alloy would not be sufficient, in order to prevent or even suppress inflammation, for example the periimplantitis.

The arrangement according to the invention therefore resembles a qualified mean, which may be provided as an independent implant or in combination with other implants easily and without any elaborate modifications of other implants, and is suitable for not causing any inflammation as for example periimplantitis and suppressing or combating inflammation possibly caused by other implants after implantation. The arrangement according to the invention may also be used prophylactically to prevent inflammation at dental implants or at implants at other locations of the body.

For example, the arrangement according to the invention may be placed directly adjacent, or in the proximity of, an inflamed tissue, or a potentially inflammation threatened tissue, for example bone, by having a preferred form or by introducing it in multiple layers or by loose unwinding and arranging.

In one embodiment the magnesium alloy comprises a silver content smaller than 12%, preferably between 6% and 10%, whereby the percentage relates to weight percentage. Silver too, does possess such an antibacterial effect. With a rapid corrosion of the magnesium alloy according to the present invention silver ions are released in a sufficient quantity, which are then resorbed by the surrounding mucous membrane and there, as previously described, release their antibacterial affect in the animate being. During release of silver ions the antibacterial protection affects around the location of the arrangement according to the invention. In order to achieve a good protection against infections, in particular periimplantitis or perimucositis, but also other inflammations, the arrangement should be located within the proximity of the center of inflammation, for example for dental inflammations close to the gum ridge and thus close to the location of a possible infection. Modifying the silver content a desired antibacterial effect may be allotted.

In one embodiment the magnesium alloy comprises an iron content greater than 100 ppm. Usually, among resorbable magnesium alloys, it is pursued to keep the content of contaminations such as iron or others as low as possible, in order to achieve a slow degradation and thus gain a long lasting supporting effect of the implants mostly used for stabilizing bones. Surprisingly though it was revealed that, a rapidly corroding magnesium alloy is advantageous, if instead of a supporting effect an antibacterial effect of the degrading substances, as an effect of the implant, is designed. A magnesium alloy with such a high iron content represents a rapidly corroding magnesium alloy according to the present invention and is thus well suitable for a release of hydrogen gas and silver ions. In a further embodiment the iron content is higher than 150 ppm, in another embodiment it is higher than 200 ppm. In an especially preferred embodiment the iron content is higher than 250 ppm. Modifying the iron content can regulate the per time unit via corrosion released quantity of hydrogen gas respectively silver ions in order to receive a necessary amount for combating the respective inflammation. Iron as additive for corrosion control is advantageous compared to other additives with similar effects, as iron is naturally resorbable and thus causes no further damage in an animate being with its presence.

In a further embodiment the iron content is smaller than 1%. Thus the magnesium alloy remains soluble in a body environment and therefore still represents a resorbable material. In a preferred embodiment the iron content is smaller than 0.5%, in a particularly preferred embodiment the iron content is smaller than 0.1%. The previously mentioned percentages relate to weight percentages. Solubility of iron in magnesium rises with temperature at which the alloy was produced.

In a further embodiment the magnesium alloy comprises a copper content greater than 0.1%. Usually, it is attempted, among absorbable magnesium alloys, to minimize contaminations such as copper or others as much as possible, in order to gain a slow degradation and thus a long lasting supporting effect of the implants mostly used for stabilizing bones. Surprisingly though it was revealed that, a rapidly corroding magnesium alloy is advantageous, if instead of a supporting effect an antibacterial effect of the degrading substances, as an effect of the implant, is designed. A magnesium alloy with not such a small content of copper represents a rapidly corroding magnesium alloy according to the present invention in relation to a magnesium alloy without a copper content and is thus basically suitable for releasing hydrogen gas and also, if needed, additionally present silver ions. Starting with a copper concentration above 0.1% an effect on corrosion is determinable. In a further embodiment the copper content is greater than 0.3%. From this stadium of copper concentration distinctly more rapid corroding magnesium alloys are achievable, leading to the advantageous corrosive characteristics securing an effective antibacterial effect of the degradation products. A magnesium alloy with such a high concentration of copper represents a very rapidly corroding magnesium alloy according to the present invention in comparison to a magnesium alloy without a copper content and is thus especially well-suited for the release of hydrogen gas and also, where appropriate, additional silver ions. In another embodiment copper content is greater than 0.6%. In an especially preferred embodiment copper content is greater than 1.0%. Previously mentioned percentages relate to weight. Modifying copper content can regulate the per time unit via corrosion released quantity of hydrogen gas respectively silver ions in order to receive a necessary amount for combating the correlating inflammation. Copper used as an additive to regulate corrosion is advantageous compared to other additives, since copper is naturally absorbed by the body of an animate being and it leaves no damages through its presence in an animate being.

In a further embodiment copper content is lower than 10%. Thus the magnesium alloy remains soluble in a body environment and therefore still represents a resorbable material. In a preferred embodiment the copper content is smaller than 5%, in a particularly preferred embodiment the copper content is smaller than 2%. The previously mentioned percentages relate to weight percentage. Solubility of copper among magnesium rises with the temperature at which the alloy was produced.

The previously mentioned alloys containing copper may also contain iron contents. For example, previously mentioned magnesium alloys with previously specified copper content can contain an iron content greater than 100 ppm, preferred greater than 150 ppm, especially preferred greater than 200 ppm, even more preferred greater than 250 ppm. Here, iron content may be smaller than 1%, preferably smaller than 0.5%, especially preferably smaller than 0.1%.

In a further embodiment the magnesium alloy contains as an additive one or more elements from the group Al, Zn, Si, Mn, Ca, Li, Sn, Sr and/or P with a respective content smaller than 1%, preferably smaller than 0.6%, especially preferred smaller than 0.2% and a total content smaller than 2%, preferably smaller than 1.5%, especially preferred smaller than 0.4%. Previously mentioned percentages relate to weight percentages. Previously mentioned additives are compatible with biomedical applications. Adding these supplements in specified amounts allows provide to the magnesium alloy with an improved robustness and greater ductility of the, without weakening antibacterial effect of the magnesium alloy. For example, adding lithium improves ductility of magnesium in a respective alloy. Adding aluminum should not be exaggerated as excessive aluminum concentrations are linked with Alzheimer's disease.

In a further embodiment the magnesium alloy comprises as an additive one or more elements from the group of Sc, Y, La, Ce, Pr, Nd, Pm, Sm, Eu, Gd, Tb, Dy, Ho, Er, Tm, Yb, and/or Lu with a respective content smaller than 4.5%, preferably smaller than 2%, especially preferred smaller than 0.15%, whereby the total content remains smaller than 7.5%, preferably smaller than 5%, especially preferred smaller than 0.4%. Previously mentioned percentages relate to weight. Rare earths basically have a high solubility in a magnesium alloy and improve mechanical characteristics of the magnesium alloy, for example its robustness and mechanical capacity, which is especially important among implants.

In a further embodiment the magnesium alloy comprises zircon with a content smaller than 0.5%. Previously mentioned percentages relate to weight percentages. Zircon reduces the actual grain size in magnesium alloys, especially in non-AL containing magnesium alloys. Zircon content is upwardly limited, since an excessive content of zircon during production of the magnesium alloy leads to a generation of Mg—Fe particles in the melt which are precipitating from the melt, which unwantedly would reduce the iron content of the magnesium alloy.

In a further embodiment the magnesium alloy comprises one or more elements from the group Co, Ni, with a respective content of less than 100 ppm, preferably less than 50 ppm and/or Be with a content smaller than 20 ppm, preferably smaller than 4 ppm. For example, nickel is not biocompatible. Beryllium is extremely toxic and should have the smallest possible content in the magnesium alloy. Beryllium traces are sometimes observed during production of pure magnesium as beryllium prevents oxidization of magnesium in the melt.

In one embodiment the arrangement is designed as either springy elastic or ductile. An elastic arrangement, in particular the structural element, enables the arrangement to be put over a form, for it to be solidly fixed on the outside of the form or for it be compressible, or for the arrangement to be inserted into an outer form, so that the arrangement is solidly placed in the outer form, after an elastic expansion. Here, elasticity is determined by its cross section, diameter of the arrangement, or of the structural element respectively, temperature at use and composition of the material. Alternatively, the structural element may be designed as ductile, in order to be inserted dimensionally stable into a predetermined position. Dimensionally stable describes a characteristic of the structural element without the influence of an external force, only the effect of its own weight affects its form not at all or only minimally. Ductility describes a characteristic of a material to change its shape plastically prior to the material collapsing under a load. A magnesium alloy given in a monocrystalline form or a nearly monocrystalline form is springly elastic. Here, the texture of the structural element from a magnesium alloy plays a significant role in the extent of its elasticity. Texture may be controlled during material production as such, but also by subsequent forming processes as extrusion and drawing processes in the course of producing the structural element. By using so called Bridgeman apparatus, Magnesium monocrystals may be grown In a further embodiment the structural element is designed as a flexible thread with a diameter smaller than 0.6 mm, preferably between 0.1 mm and 0.4 mm. Over a diameter of 0.6 mm the arrangement is to thick and thus unmanageable for its use as an implant respectively additive for an implant, in particular if prevention of periimplantitis for dental implants is desired. For example, the arrangement has a diameter of 0.3 mm. The diameter describes the lateral expansion of the structural element respectively the arrangement perpendicular to its length.

In another embodiment the arrangement is a seamed material. Here, the same applies for its diameter, as an arrangement of a suture material. Threads of magnesium alloys as arrangement respectively structural element are, for example, produced using wire drawing or extrusion. Here, solid or viscous hardenable materials are continuously either drawn or pressed from a forming opening under pressure. This creates the resulting bodies with a cross section of the opening in generally any desired length.

In a further embodiment the structural element is designed as a dimensionally stable form with at least rounded edges. Dimensionally stable bodies may be produced using punching or laser cutting with a high velocity, and according to the respective process design can be produced parallely in high quantities with a single punch or a single laser- or hydro-jet cutting process, from a respective plate of the magnesium alloy of the arrangement, or the structural element respectively.

In a further embodiment the dimensionally stable form possesses a circular form with a gap and two endings facing the gap, whereby at each ending a pull or thrust means is arranged, in order to at least temporarily enlarge or decrease the gap using a pulling or thrusting force at the pull or thrust means of the structural element. This enables an elastic arrangement, in particular the structural element, in spite of the dimensionally stable form, to be widened with a thrusting force and later put over another form, for example another tooth of a patient, in order for the arrangement to then be solidly fixed on this form, for example a tooth, without any pulling force. This also enables the elastic arrangement, in particular the structural element, in spite of the dimensionally stable form, decreases using a thrust force and then is inserted into the other form with an undercut, in order for the arrangement to solidly sit within this form, for example a tooth pocket, with no compressive force needed.

In one embodiment the structural element comprises an outer coating with a thickness smaller or equal to 15 μm, in particular smaller or equal to 10 μm. The coating call additionally comprise an antibacterial effect and/or may serves to produce a smooth surface on the arrangement or the structural element. An antibacterial coating may cause a controlled release of biofunctional substances, which supports the healing process. The coating may also be made of a material from the group of native or artificial collagens, fibrins, fibroins, natural or artificial silk, natural proteins or polymers polylactic acid (PLA), poly(D-lactic acid) (PDLA) and poly(L-lactic acid) (PLLA), synthetic polymers such as polytetrafluoroethylene (PTFE) and phosphinocarboxylic acid (PCA), a sol-gel layer or an oxide layer, for example produced via plasma-electrolytic oxidation. Such a coating can protect the arrangement or the structural element, respectively or modify its surface characteristics.

In a further embodiment the arrangement fulfills the function of a skin expander. Tissue- or skin expanders are used to obtain skin for transplantation from, for example, in cases of burns or accidents. These are then primarily used for reconstruction, thus in restoration. An expander is inserted like a temporary implant. Usually an expander is an empty casing with an added valve, which is gradually filled with saline or air. A slow stretching of the skin within weeks or months produces additional tissue, which may then be transplanted to another location of a patient. A disadvantage of ordinary expanders is the fact that the implant needs to be removed after stretching the skin. This may take place during skin transplantation, but represents a further procedure during this surgery. Especially to a disadvantage is the permanent presence of a catheter during stretching for filling the case, increasing the risk of an infection due to the permanent skin puncture. Newly, the risk of an infection is reduced with a case or a swelling pad with an injection membrane, as no permanent entry needs to be present and filling occurs through recurrent injections with a needle. Nonetheless, recurring injections with a needle pose a greater infection risk, in particular for patients with a naturally high risk, for example victims of burnings, who often need a skin transplantation. According to the invention the problem is solved by the presented arrangement in form of a structural element made from a rapidly corroding magnesium alloy, implanted at a fitting location under the skin, causing a bubble which expands the skin, by creating hydrogen gas for a defined time span. Thus, the arrangement works like an expander without the usual risks. For example, the arrangement may be a loosely uncoiled thread, inserted through a small cut under the skin of a patient, which is closed after insertion, or the arrangement may be a structural element with an dimensionally stable form, for example spiral shaped structure, made from a plate or a foil using punches or laser cutting. This arrangement further comprises the previously described antibacterial effect, reducing the already diminished risk of infection to a minimum.

In a further embodiment the arrangement comprises further flexible threads, whereat the further threads and the structural element are arranged parallel along their center lines and symmetrically to each other as a thread shaped arrangement, whereat the structural element is also designed as a flexible thread. The resulting arrangement is thus also thread shaped and flexible. The further threads may thus protect the structural element or add their own functions to those of the structural element, as for example a better use during specific fractures, which need a torn ligament attached back to a bone and the arrangement may serve as a very solid cord or knot with an additional antibacterial effect, or if a specific mobility for inserting a structural element is required. In one embodiment all threads are designed as structural elements, according to the invention, and twisted together, increasing mechanic stability of the arrangement.

In a further embodiment the structural element is designed as a center thread and the further threads as a first outer case in a symmetrical and parallel arrangement of the further threads to each other around the structural element. Characteristics of the further threads towards the structural element as a center thread may be coordinated. In particular, pace of resorption of magnesium from the magnesium alloy may be regulated by further desired threads. For example, several of the further threads may be produced as a structural element of the magnesium alloy, in order to increase the release of silver to the surrounding mucous tissue according to severity of the inflammation, or further threads with a lower silver content, or no silver at all, for reducing silver release, may be arranged around the structural element. In a further embodiment of the thread like arrangement further threads as a second outer case are comprised, whereat these further threads, along their center lines, are aligned symmetrically and parallel to each other around the first casing. Here, at least some of these further threads may be made of a thread material different to the material of the structural element, preferably the thread material is made from a material from the group of native or artificial collagens, fibrin, fibroin, natural or artificial silk, natural proteins or polymers PLA, PDLA, PLLA, PTFE or PCA or the thread material is at least on its surface an oxidized material of the structural element, preferably done with plasma electrolytic oxidation. This surface oxidization layer passivates the magnesium alloy of the structural element towards environmental effects from outside the structural element. The oxidization layer may be produced artificially or may have grown naturally. An artificial oxidization layer can, for example, be applied using anodization or plasma electrolytic oxidation (PEO). Plasma electrolytic oxidation (PEO) is also known as plasma chemical oxidation, anodization is known as spark formation (ANOF) or so called micro-arc oxidation (MAO). A naturally grown oxidization layer may have grown under air or in a gas with regulated oxygen. The preferred thickness of this oxidization layer is not bigger than 10 μm. With magnesium alloys this oxidization layer may prevent dispersion of the structural element in a watery environment or control the timeline of a dispersion process, which may be critical according to application, for example with arrangements according to the invention used as implants. Further threads from the second casing may serve with an aesthetic function, as these further threads made of a polymer, for example PTFE, are skin colored or in the color of a respective tooth. This method allows an inconspicuous appearance to the outside. The further threads of the first casing may, for example, obtain the desired antibacterial characteristics of the arrangement according to the invention. Here, the further threads of the first casing may have an arbitrary color, as these are covered from the second casing and are not visible.

In a further embodiment the further threads of the first and/or second casing are twisted around the structural element serving as the center thread. This increases the mechanical stability of the arrangement during storage, transport and handling during a respective application.

The invention further relates to a mount with an arrangement carried by the mount comprising at least one structural element made of a resorbable material with an antibacterial effect, whereby the arrangement is designed as a flexible thread shaped arrangement with a form with an aspect ratio greater 100, and the mount is designed to produce, applying cutting to the material of the arrangement, separate arrangements in a desired length with a smaller aspect ratio, for example an aspect ratio of 10. Here the arrangement is also a thread shaped arrangement which is accordingly longer. The mount may be a roll, onto which the arrangement is wound. Cutting may be performed with a scissor or a knife.

SHORT DESCRIPTION OF FIGURES

Figure 2:
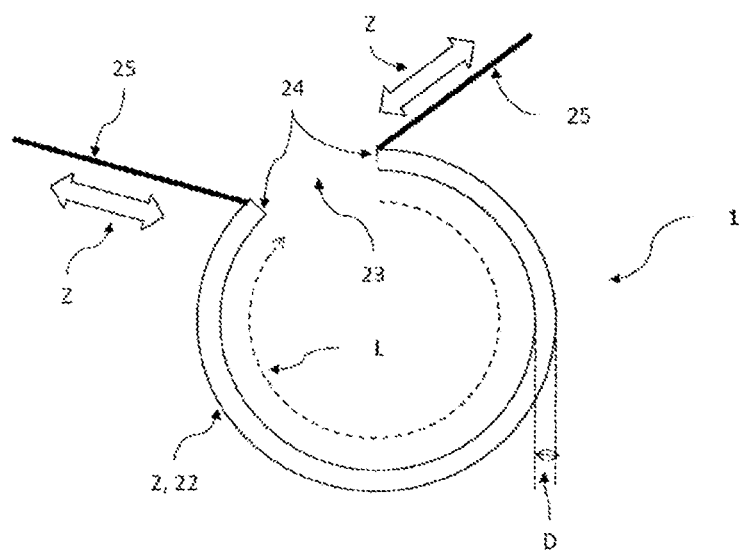
Figure 3:
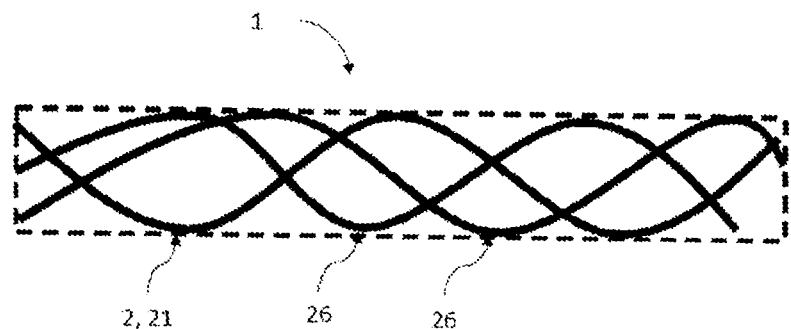
Figure 4:
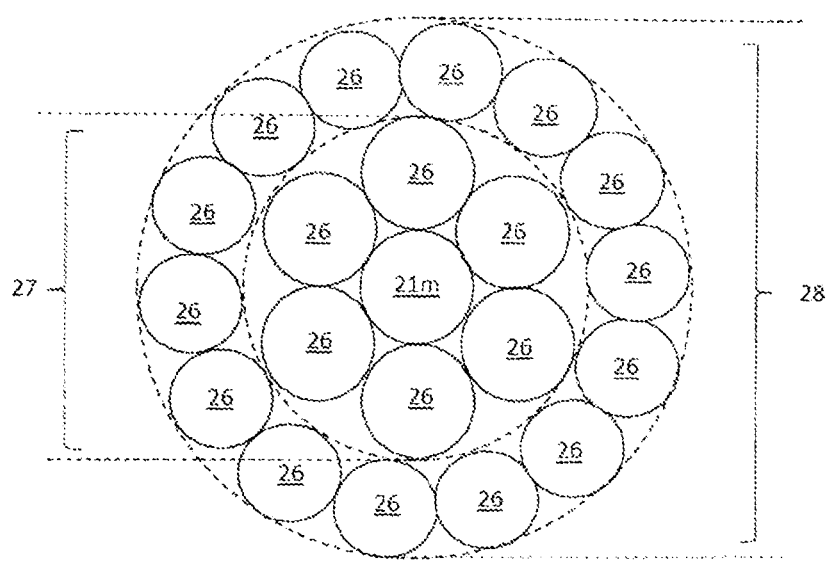
Figure 5:
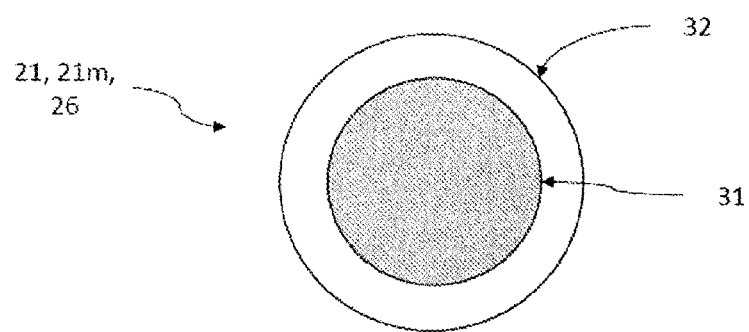
Figure 6:
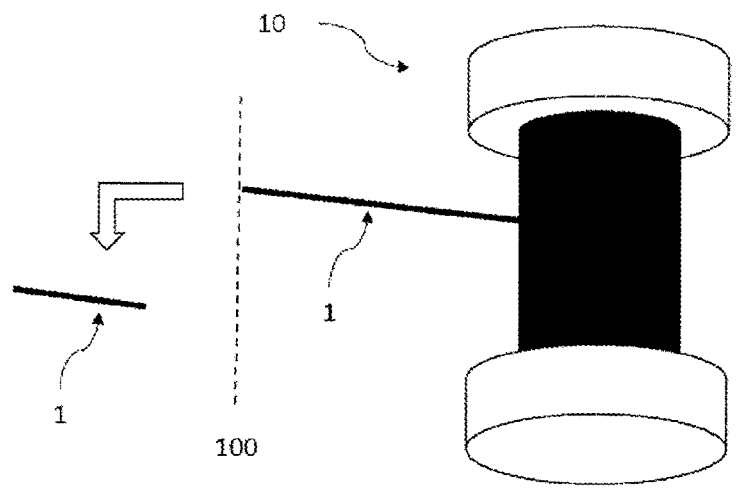
Figure 7:
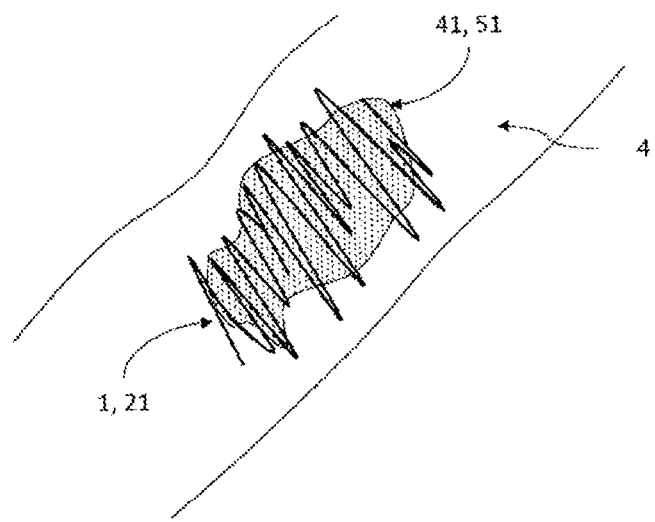
Figure 8:
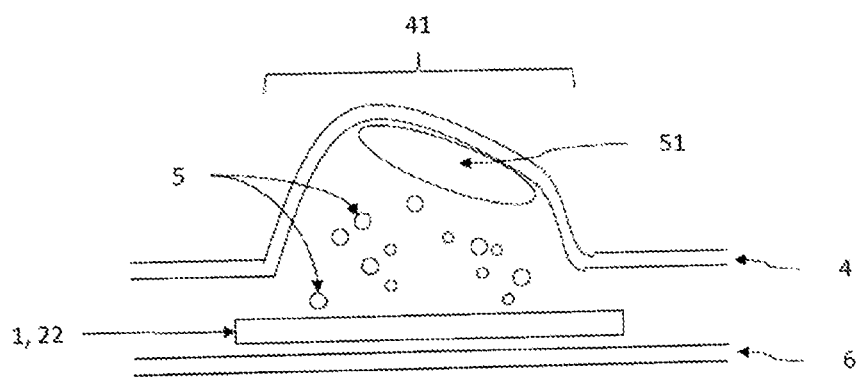

These and other aspects of the invention are shown in detail in the figures as follows:

FIG. 1: An embodiment of the arrangement according to the invention with a flexible thread shaped structural element;

FIG. 2: An embodiment of the arrangement according to the invention with a dimensionally stable circular structural element;

FIG. 3: An further embodiment of the arrangement according to the invention comprising a structural element as thread and further threads, all twisted together;

FIG. 4: A sectional view through an embodiment of the arrangement according to the invention with further threads, arranged around the structural element as a center thread;

FIG. 5: An embodiment of a thread of the arrangement according to the invention with an inner core and an outer coating;

FIG. 6: An embodiment of a mount according to the invention with a mounted arrangement according to the invention;

FIG. 7: The arrangement according to the invention as a tissue- or skin expander or as an antibacterial implant in form of a thread viewed from above the skin;

FIG. 8: The arrangement according to the invention as a skin expander with an dimensionally stable form in a sectional view through skin, from the side.

DETAILED DESCRIPTION OF THE EXAMPLES

FIG. 1 depicts an embodiment of the arrangement 1 according to the invention, with a flexible thread shaped structural element 2, 21 made of a resorbable material with an antibacterial effect. The structural element has the shape of a thread 21 with an aspect ratio greater than 10, whereat the diameter is between 0.1 mm and 0.4 mm. The aspect ratio is the ratio between length L of thread 21 and diameter D of thread 21. Material of structural element 2, 21 is a rapidly corroding magnesium alloy with a silver content between 6% and 10% and an iron content greater than 100 ppm and smaller than 1%. In a further embodiment the iron content may be between 250 ppm and 0.5%. The thread may have an outer coating with a thickness smaller than or equal to 10 μm. In another embodiment the material of the structural element 2,21 is a rapidly corroding magnesium alloy, for example, with a silver content between 6% and 10% and with a copper content of at least 0.1%, better greater than 0.3% and smaller than 10%. In other embodiments the copper content may lie between 0.6% and 5%.

The magnesium alloy of structural element 2,21 may have, as an additive one or more elements from the group Al, Zn, Si, Mn, Ca, Li, Sn, Sr and/or P with a respective content smaller than 1%, preferably smaller than 0.6%, especially preferred smaller than 0.2% and a total content smaller than 2%, preferably smaller than 1.5%, especially preferred smaller than 0.4%, or one or more elements from the group of Sc, Y, La, Ce, Pr, Nd, Pm, Sm, Eu, Gd, Tb, Dy, Ho, Er, Tm, Yb, and/or Lu with a respective content smaller than 4.5%, preferably smaller than 2%, especially preferred smaller than 0.15%, whereat the total content remains smaller than 7.5%, preferably smaller than 5%, especially preferred smaller than 0.4%. Previously mentioned percentages relate to weight percentages. In a further embodiment the magnesium alloy comprises one or more elements from the group Co, Ni, with a respective content of less than 100 ppm, preferably less than 50 ppm and/or Be with a content smaller than 20 ppm, preferably smaller than 4 ppm.

FIG. 2 depicts an embodiment of arrangement 1 according to the invention with an dimensionally stable circular structural element 2,22 also made of a resorbable material with an antibacterial effect. Structural element 2,22 has a spring elastic circular form 22 with rounded edges mit a gap 23 and two endings 24 facing the gap 23. At these endings 24 is a respective pull-resp. thrust instrument 25 arranged, in order to enlarge or reduce the gap using a pull-resp. thrust force Z on the pull-resp. thrust means 25 of structural element 2 at least temporarily to ease installation respectively positioning of the arrangement. The aspect ratio is the ratio between length L of circular form along its elongation and diameter D of circular form 22. Material of structural element 2, 22 is a rapidly corroding magnesium alloy with a silver content between 6% and 10% and an iron content greater than 100 ppm and smaller than 1%. In a further embodiment the iron content may be between 150 ppm and 0.5% or between 250 ppm and 0.1%. In another embodiment the material of the structural element 2,22 is a rapidly corroding magnesium alloy, for example, with a silver content between 6% and 10% and with a copper content of at least 0.1%, better greater than 0.3% and smaller than 10%. In other embodiments the copper content may lie between 0.6% and 5%. The circular form 22 may possess an outer coating with a thickness smaller than or equal to 10 μm.

The magnesium alloy of structural element 2,22 contains as an additive one or more elements from the group Al, Zn, Si, Mn, Ca, Li, Sn, Sr and/or P with a respective content smaller than 1%, preferably smaller than 0.6%, especially preferred smaller than 0.2% and a total content smaller than 2%, preferably smaller than 1.5%, especially preferred smaller than 0.4%, or one or more elements from the group of Sc, Y, La, Ce, Pr, Nd, Pm, Sm, Eu, Gd, Tb, Dy, Ho, Er, Tm, Yb, and/or Lu with a respective content smaller than 4.5%, preferably smaller than 2%, especially preferred smaller than 0.15%, whereat the total content remains smaller than 7.5%, preferably smaller than 5%, especially preferred smaller than 0,4%. Previously mentioned percentages relate to weight percentages. The magnesium alloy may also comprise zircon with a content smaller than 0.5%. The magnesium alloy may also comprise one or more elements from the group Co, Ni, with a respective content of less than 100 ppm, preferably less than 50 ppm and/or Be with a content smaller than 4 ppm.

FIG. 3 depicts a further embodiment of arrangement 1 according to the invention comprising structural element 2 as a flexible thread 21 and further flexible threads 26, whose center line is parallel and symmetrical to each other as a thread shaped arrangement 1, whereby structural element 2,21 and threads 26 are twisted together.

FIG. 4 depicts a sectional view perpendicular to the length of arrangement 1 through an embodiment of arrangement 1 according to the invention with further threads 26, arranged around structural element 2 as a center thread 21m, as a first casing 27 in a symmetrical and parallel arrangement together around structural element 21m. Additionally to first casing 27, the thread shaped arrangement 1 comprises further threads 26 as a further second casing with a symmetrical and parallel arrangement of further threads 26 to each other around first casing 27. Here, at least some of the further threads 26 or where necessary all other threads are made of a material different to that of structural element 21m. Thread material of further threads 26 is made from a material from the group of native or artificial collagens, fibrin, fibroin, natural or artificial silk, natural proteins or polymers PLA, PDLA, PLLA, PTFE or PCA or the thread material is at least on its surface an oxidized material of the structural element 2, preferably done with plasma electrolytic oxidization. In a not depicted embodiment further threads 26 of the first and/or second casing 27,28 may be twisted around structural element 2 as the center thread 21m. In a further embodiment threads from casing one and two may be made of a magnesium alloy or at least comprise one. In an alternative arrangement to FIG. 4 threads 21m,26 may be arranged reversibly, so a further thread 26 may be arranged as a central thread (analogous to center threat 21m in FIG. 4) around structural element 2 as an arrangement of threads (analogous to further threads in FIG. 4) in a first outer casing 27 in a symmetrical and parallel arrangement to each other around the central thread. The central thread may guarantee firmness respectively stability for the arrangement, while the arrangement of threads of structural element 2 around the central thread display their antibacterial effect.

FIG. 5 depicts an embodiment of a thread 21, 21m, 26 of the arrangement according to the invention with an inner core 31 as a carrying structure and an outer coating 32. The inner core 31 may be made of the magnesium alloy of the structural element or also as a further thread 26 in some execution examples of a different material. The outer coating 32 may be made of a different material to that of core 31. Suited materials for a structure depicted in FIG. 5 (core 31, outer coating 32) are, for example, described in combination of FIG. 1 and 4. For example, the inner core 31 may be made of a magnesium alloy according to the invention with a first composition and outer coating 32 may also be made of a magnesium alloy with a second composition not equal to the first.

FIG. 6 depicts an embodiment of a mount 10 according to the invention with a mounted arrangement 1 according to the invention, which comprises at least one structural element 2 made of a resorbable material with an antibacterial effect, whereat arrangement 1 is designed as a flexible thread shaped arrangement with a form with an aspect ratio bigger than 100, and where the mount 10 is designed, while applying cutting 100 of the material of the arrangement 1, to create separate arrangements with a desired with smaller aspect ratios. The dotted line hints to cutting 100, for example with a scissor or knife.

FIG. 7 depicts arrangement 1 according to the invention as a tissue- or skin expander in form of a thread 21 viewed from above on the skin 4. Here arrangement 1 was inserted (implanted) under the patient's skin as a randomly uncoiled flexible thread 21, through a small cut which was afterwards closed. The rapidly corroding magnesium alloy of arrangement 1 should on location produce excessive hydrogen gas (not shown here, see FIG. 8) during a defined timeline at the expandable area 41 in form of a bubble 51.

FIG. 7 depicts alternative arrangement 1 according to the invention as an antibacterial implant in form of thread 21 in a perspective "through" the skin resp. a top view on bone 4. Here, arrangement 1 is designed as a randomly decoiled flexible thread 21, pushed through a small cut (implanted) in the patient's skin, which was later closed. The rapidly corroding magnesium alloy of arrangement 1 is supposed to have an antibacterial effect by producing hydrogen gas and optionally releasing silver ions over a defined timeline towards infected area 41 of bone 4.

FIG. 8 depicts arrangement 1 according to the invention as a skin expander with a dimensionally stable form 22 in a sectional view from the side through skin 4. The dimensionally stable form 22 is, for example, a spiral made from a plate or a foil using punches or laser cutting, which is inserted under the skin through a cut (implanted), which is later closed. As also seen in the embodiment of FIG. 7, the rapidly corroding magnesium alloy excessively produces hydrogen gas 5, which ascends and creates a bubble 51 of hydrogen gas 5 over a defined time period without any further procedure, which thus expands skin 4. Layer 6 below arrangement 1 represents subcutaneous tissue.

The arrangements according to FIGS. 7 and 8 comprise an antibacterial effect due to excessive hydrogen gas production, which even further decreases the already diminished risk of infection for this embodiment of a skin expander.

The embodiments depicted here represent only examples of the present invention and must not be understood as limiting. Alternatives taken into consideration by the person skilled in the art are similarly comprised by the scope of the present invention.

REFERENCES

1 Arrangement according to the invention
2 Structural element according to the arrangement of the invention
21 Structural element as flexible thread
21m Structural element as flexible center thread
22 Structural element as dimensionally stable structure
23 Gap in dimensionally stable structural element
24 Endings of structural element
25 Pull means on dimensionally stable structural element
26 Further threads in the arrangement according to the invention
27 First casing of further threads in the arrangement according to the invention
28 Second casing of further threads in the arrangement according to the invention
31 Inner core of a thread of the arrangement according to the invention
32 Outer layer of a thread of the arrangement according to the invention
4 Skin or bone
41 Stretchable or stretched area of skin or inflamed are of bone, repsectively
5 Hydrogen gas
51 Hydrogen gas bubble 6 Subcutaneous tissue
10 Mount, for example a roll
100 Cutting of arrangement carried on mount
D. Diameter of structural element
L. Length of structural element
Z. Pull force

The invention claimed is:

1. An arrangement for use as a tissue expander, skin expander or implant comprising at least one structural element made of an absorbable material with an antibacterial effect having a shape which has an aspect ratio greater than 10,
wherein the material is a rapidly corroding magnesium alloy, which has:
a. a silver content by weight of between 6% and 12%; and
b. an iron content by weight of between 0.01% and 1% or a copper content by weight of between 0.1% and 10%; and
wherein the structural element is a dimensionally stable structure having at least partially rounded edges,
wherein the dimensionally stable structure has a circular structure with a gap and two endings facing the gap, and
wherein at the two endings, respectively, either a pull instrument or a thrust instrument is arranged for either temporarily enlarging or minimizing the gap using a pull force or a thrust force at the pull instrument or the thrust instrument.

2. The arrangement according to claim 1, wherein the magnesium alloy comprises a silver content by weight of between 6% and 10%.

3. The arrangement according to claim 1, wherein the magnesium alloy comprises an iron content by weight that is greater than 150 ppm and less than 1%.

4. The arrangement according to claim 1, wherein the magnesium alloy comprises an iron content by weight of between 0.025% and 0.5%.

5. The arrangement according to claim 1, wherein the magnesium alloy comprises a copper content by weight that is greater than 0.3% and less than 10%.

6. The arrangement according to claim 5, wherein the magnesium alloy comprises a copper content by weight that is greater than 0.1% and less than 5%.

7. The arrangement according to claim 1, wherein the magnesium alloy contains:
a. one or more than one element selected from the group consisting of Al, Zn, Si, Mn, Ca, Li, Sn, Sr and P in a respective content by weight of less than 1%; or
b. one or more than on element selected from the group consisting of Sc, Y, La, Ce, Pr, Nd, Pm, Sm, Eu, Gd, Tb, Dy, Ho, Er, Tm, Yb and Lu in a respective content by weight of less than 4.5%.

8. The arrangement according to claim 1, wherein the magnesium alloy contains one or more than one element selected from the group consisting of Co and Ni in a respective content by weight of less than 100 ppm.

9. The arrangement according to claim 1, wherein the structural element is a flexible thread with a diameter smaller than 0.6 mm, and wherein the arrangement is a suture material.

10. The arrangement according to claim 1, wherein the structural element has an outer coating with a thickness smaller or equal to 15 μm, wherein the outer coating is made of a material selected from the group consisting of:
a. collagens;
b. fibrins;
c. fibroins;
d. natural or artificial silk;
e. natural proteins or polymers;
f. polylactic acid (PLA);
g. poly(D-lactic acid) (PDLA);
h. poly(L-lactic acid) (PLLA);
i. polytetrafluoroethylene (PTFE);
j. phosphinocarboxylic acid (PCA);
k. a sol-gel layer; and
l. an oxide layer.

11. The arrangement according to claim 1, wherein the structural element is in a form of a flexible thread, wherein the arrangement further comprises further flexible threads, and wherein the further flexible threads and the structural element are arranged parallel and symmetric on their respective center lines as a thread shaped arrangement.

12. The arrangement according to claim 11, wherein either:
a. all threads in the arrangement are structural elements and are twisted together; or
b. the structural element is a center thread and the further flexible threads are a first outer casing arranged in a symmetrical and parallel arrangement along their respective center lines together around the structural element.

13. The arrangement according to claim 12, wherein at least some of the further flexible threads are made of a thread material that is different than the material of structural element.

14. The arrangement according to claim 12, wherein the further flexible threads of the outer casing are twisted together around the structural element.

15. A mount with an arrangement carried by the mount comprising at least one structural element made of an absorbable material with antibacterial effect according to claim 1, wherein the arrangement carried by the mount is a flexible thread shaped arrangement having an aspect ratio greater than 100, and wherein the arrangement carried by the mount is configured to be cut into separate arrangements having a desired length and a smaller aspect ratio.

16. An arrangement comprising at least one structural element made of an absorbable material with an antibacterial effect having a shape which has an aspect ratio greater than 10,
wherein the material is a rapidly corroding magnesium alloy, which has:
a. a silver content by weight of between 6% and 12%; and
b. an iron content by weight of between 0.01% and 1% or a copper content by weight of between 0.1% and 10%, and
wherein the arrangement is a tissue or skin expander.

* * * * *

UNITED STATES PATENT AND TRADEMARK OFFICE
CERTIFICATE OF CORRECTION

PATENT NO. : 11,547,775 B2
APPLICATION NO. : 16/474597
DATED : January 10, 2023
INVENTOR(S) : Alexander Kopp et al.

It is certified that error appears in the above-identified patent and that said Letters Patent is hereby corrected as shown below:

In the Claims

In Column 13, Line 49, Claim 7: Change "on" to --one--

Signed and Sealed this
Twenty-first Day of March, 2023

*Katherine Kelly Vidal*

Katherine Kelly Vidal
*Director of the United States Patent and Trademark Office*